(12) United States Patent
Hein et al.

(10) Patent No.: US 10,595,782 B2
(45) Date of Patent: Mar. 24, 2020

(54) MICRO INDUCTION POSITION SENSOR

(71) Applicant: Boston Scientific Scimed Inc., Maple Grove, MN (US)

(72) Inventors: Matthew Hein, Eden Prairie, MN (US); Mark Kringle, Minneapolis, MN (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 254 days.

(21) Appl. No.: 15/384,230

(22) Filed: Dec. 19, 2016

(65) Prior Publication Data

US 2017/0172509 A1    Jun. 22, 2017

Related U.S. Application Data

(60) Provisional application No. 62/270,016, filed on Dec. 20, 2015.

(51) Int. Cl.
| | |
|---|---|
| *A61B 5/00* | (2006.01) |
| *A61B 5/042* | (2006.01) |
| *A61B 18/14* | (2006.01) |
| *A61B 90/00* | (2016.01) |
| *A61B 17/00* | (2006.01) |
| *A61B 18/00* | (2006.01) |

(52) U.S. Cl.
CPC ............ *A61B 5/6885* (2013.01); *A61B 5/042* (2013.01); *A61B 18/1492* (2013.01); *A61B 2017/00039* (2013.01); *A61B 2017/00075* (2013.01); *A61B 2018/00577* (2013.01); *A61B 2018/00767* (2013.01); *A61B 2090/064* (2016.02); *A61B 2090/065* (2016.02); *A61B 2505/05* (2013.01); *A61B 2562/0223* (2013.01); *A61M 2205/332* (2013.01)

(58) Field of Classification Search
CPC ..... A61B 5/042; A61B 5/6846; A61B 5/6847; A61B 5/6885; A61B 18/1492
See application file for complete search history.

(56) References Cited

U.S. PATENT DOCUMENTS

| | | |
|---|---|---|
| 5,383,874 A | 1/1995 | Jackson et al. |
| 5,647,870 A | 7/1997 | Kordis et al. |
| 5,836,990 A | 11/1998 | Li |
| (Continued) | | |

FOREIGN PATENT DOCUMENTS

| | | |
|---|---|---|
| DE | 102009037044 A1 | 3/2011 |
| EP | 1169974 A1 | 1/2002 |
| (Continued) | | |

OTHER PUBLICATIONS

International Search Report and Written Opinion issued in PCT/US2016/067629, dated Mar. 17, 2017, 13 pages.

(Continued)

*Primary Examiner* — Max F Hindenburg
(74) *Attorney, Agent, or Firm* — Faegre Drinker Biddle & Reath LLP

(57) ABSTRACT

A catheter includes a proximal segment and a distal segment. The catheter is configured to permit relative movement between the distal segment and the proximal segment in response to an application of force on the distal segment. The catheter further includes an inductive sensing element configured to measure displacement between the proximal segment and the distal segment.

17 Claims, 6 Drawing Sheets

(56) References Cited

U.S. PATENT DOCUMENTS

| | | |
|---|---|---|
| 5,904,680 A | 5/1999 | Kordis et al. |
| 5,911,694 A | 6/1999 | Ikeda et al. |
| 6,152,899 A | 11/2000 | Farley et al. |
| 6,695,808 B2 | 2/2004 | Tom |
| 7,637,903 B2 | 12/2009 | Lentz et al. |
| 7,720,420 B2 | 5/2010 | Kajita |
| 8,374,670 B2 | 2/2013 | Selkee |
| 8,529,476 B2 | 9/2013 | Govari |
| 9,125,565 B2 * | 9/2015 | Hauck .................. A61B 5/0053 |
| 9,486,272 B2 * | 11/2016 | Bonyak .............. A61B 18/1233 |
| 9,510,786 B2 * | 12/2016 | Gliner .................. A61B 5/6852 |
| 9,974,608 B2 * | 5/2018 | Gliner .................. A61B 5/6885 |
| 10,022,190 B2 * | 7/2018 | Valsamis .................. A61B 5/22 |
| 2003/0069522 A1 | 4/2003 | Jacobsen et al. |
| 2003/0130615 A1 | 7/2003 | Tom |
| 2006/0189896 A1 | 8/2006 | Davis et al. |
| 2007/0156209 A1 | 7/2007 | Laufer et al. |
| 2007/0191829 A1 | 8/2007 | McGee et al. |
| 2008/0015568 A1 | 1/2008 | Paul et al. |
| 2008/0051704 A1 | 2/2008 | Patel et al. |
| 2008/0161796 A1 | 7/2008 | Cao et al. |
| 2009/0076476 A1 | 3/2009 | Barbagli et al. |
| 2009/0099551 A1 | 4/2009 | Tung et al. |
| 2009/0306650 A1 * | 12/2009 | Govari ............... A61B 18/1492 606/41 |
| 2010/0168620 A1 | 7/2010 | Klimovitch et al. |
| 2011/0160556 A1 | 6/2011 | Govari |
| 2012/0041295 A1 | 2/2012 | Schultz |
| 2012/0265102 A1 | 10/2012 | Leo et al. |
| 2012/0271135 A1 | 10/2012 | Burke et al. |
| 2013/0289369 A1 | 10/2013 | Margolis |
| 2014/0025069 A1 | 1/2014 | Willard et al. |
| 2014/0081264 A1 | 3/2014 | Fandrey et al. |
| 2014/0128949 A1 | 5/2014 | Hollett et al. |
| 2014/0276078 A1 | 9/2014 | Schweitzer et al. |
| 2014/0276787 A1 | 9/2014 | Wang et al. |
| 2015/0157400 A1 | 6/2015 | Gelbart et al. |
| 2015/0300895 A1 | 10/2015 | Matsudate et al. |
| 2015/0369373 A1 | 12/2015 | Reith et al. |
| 2016/0113582 A1 | 4/2016 | Altmann et al. |
| 2017/0035358 A1 | 2/2017 | Rankin |
| 2017/0035991 A1 | 2/2017 | Rankin et al. |
| 2017/0143416 A1 | 5/2017 | Guler et al. |
| 2017/0354467 A1 | 12/2017 | Rankin et al. |

FOREIGN PATENT DOCUMENTS

| | | |
|---|---|---|
| EP | 1803410 A1 | 7/2007 |
| EP | 2047797 A2 | 4/2009 |
| EP | 2172240 A1 | 4/2010 |
| EP | 2526887 A1 | 11/2012 |
| EP | 2662015 B1 | 11/2013 |
| EP | 2732760 A1 | 5/2014 |
| EP | 2862537 A1 | 4/2015 |
| WO | 1995010978 A1 | 4/1995 |
| WO | 2001070117 A2 | 9/2001 |
| WO | 2002021995 A2 | 3/2002 |
| WO | 2015069887 A1 | 5/2015 |

OTHER PUBLICATIONS

International Search Report and Written Opinion issued in PCT/US2017015426, dated May 10, 2017, 13 pages.

Hoffmayer, K.S., et al. "Contact Force-Sensing Catheters." Current Opinion in Cardiology, 30(1):74-80, Jan. 2015.

International Search Report and the Written Opinion issued in PCT/US2016/045303, dated Oct. 20, 2016, 15 pages.

International Search Report and Written Opinion issued in PCT/US2016/045907, dated Oct. 20, 2016, 10 pages.

International Search Report and Written Opinion issued in PCT/US2016/062976, dated Feb. 8, 2017, 12 pages.

Internatilonal Preliminary Report on Patentability issued in PCT/US2016/045303, dated Feb. 22, 2018, 9 pages.

International Preliminary Report on Patentability issued in PCT/US2016/045907, dated Feb. 22, 2018, 7 pages.

International Preliminary Report on Patentability issued in PCT/US2016/062976, dated May 31, 2018, 8 pages.

International Preliminary Report on Patentability issued in PCT/US2016/067629, dated Jul. 5, 2018, 8 pages.

International Preliminary Report on Patentability issued in PCT/US2017/015426, dated Aug. 9, 2018, 8 pages.

* cited by examiner

MICRO INDUCTION POSITION SENSOR

CROSS-REFERENCE TO RELATED APPLICATION

This application claims priority to Provisional Application No. 62/270,016, filed Dec. 20, 2015, which is herein incorporated by reference in its entirety.

TECHNICAL FIELD

The present disclosure relates generally to medical catheters.

BACKGROUND

In ablation therapy, it may be useful to assess the contact between the ablation element and the tissue targeted for ablation. In interventional cardiac electrophysiology (EP) procedures, for example, the contact can be used to assess the effectiveness of the ablation therapy being delivered. Other catheter-based therapies and diagnostics can be aided by knowing whether a part of the catheter contacts targeted tissue, and to what degree the part of the catheter presses on the targeted tissue. The tissue exerts a force back on the catheter, which can be measured to assess the contact and the degree to which the catheter presses on the targeted tissue.

SUMMARY

This disclosure is directed to techniques for measuring the relative displacement of a catheter tip using an inductive sensing element. When combined with a known resistance to displacement, such a spring constant for mounting structure of the catheter tip, the displacement measurements also provide indications of contact force on the catheter tip.

In an Example 1, a catheter comprises: a proximal segment; a distal segment, the catheter being configured to permit relative movement between the distal segment and the proximal segment in response to an application of force on the distal segment; and an inductive sensing element configured to measure displacement between the proximal segment and the distal segment.

In an Example 2, the catheter of Example 1, further comprising a spring between the proximal segment and the distal segment, wherein the inductive sensing element is configured to measure force on the distal segment based on a known resistance to the application of force on the distal segment and the measured displacement between the proximal segment and the distal segment.

In an Example 3, the catheter of Example 1 or Example 2, wherein the inductive sensing element is one of a plurality of inductive sensing elements, each of the plurality of inductive sensing elements being configured to measure displacement between the proximal segment and the distal segment.

In an Example 4, the catheter of Example 3, wherein the plurality of inductive sensing elements includes three inductive sensing elements arranged about a longitudinal axis of the catheter.

In an Example 5, the catheter of Example 3 or Example 4, wherein each of the plurality of inductive sensing elements is located within a central aperture of the spring.

In an Example 6, the catheter of Example 3 or Example 4, wherein the spring is one of a plurality of springs, and wherein each of the plurality of inductive sensing elements is located within a central aperture of one of the plurality of springs.

In an Example 7, the catheter of any of Examples 1-6, wherein the inductive sensing element is oriented to measure displacement along a direction that is about parallel to a longitudinal axis of the catheter.

In an Example 8, the catheter of any of Examples 1-7, wherein the inductive sensing element includes: a magnetic core; and conductive coil windings, the conductive coil windings being configured to move relative to the magnetic core in conjunction with movement between the distal segment and the proximal segment, wherein an inductance of the conductive coil windings changes based on its position relative to the magnetic core.

In an Example 9, the catheter of Example 8, wherein the magnetic core is substantially fixed relative to the distal segment, and wherein the conductive coil windings is substantially fixed relative to the proximal segment.

In an Example 10, the catheter of Example 8 or Example 9, wherein the inductive sensing element further includes an electrically insulating tube between the magnetic core and the conductive coil windings, wherein the conductive coil windings is mounted to the electrically insulating tube.

In an Example 11, the catheter of Example 10, wherein the conductive coil windings includes an electrical trace on the electrically insulating tube.

In an Example 12, the catheter of Example 8 or Example 9, wherein the conductive coil windings includes an insulating layer, wherein a least a portion of the insulating layer is adjacent to the magnetic core.

In an Example 13, the catheter of any of Examples 8-12, further comprising a lubricating layer between the magnetic core and the conductive coil windings.

In an Example 14, the catheter of any of Examples 1-13, wherein the distal segment includes an ablation element configured to deliver ablation therapy.

In an Example 15, a system for measuring a force, the system comprising: a catheter according to any of Examples 1-14; and control circuitry configured to receive a signal from the inductive sensing element indicative of the measured displacement and calculate a magnitude and a direction of force on the distal segment based on a known resistance to the application of force on the distal segment and the measured displacement between the proximal segment and the distal segment.

In an Example 16, a catheter comprising: a proximal segment; a distal segment, the catheter being configured to permit relative movement between the distal segment and the proximal segment in response to an application of force on the distal segment; and an inductive sensing element configured to measure displacement between the proximal segment and the distal segment.

In an Example 17, the catheter of Example 16, further comprising a spring between the proximal segment and the distal segment, wherein the inductive sensing element is configured to measure force on the distal segment based on a known resistance to the application of force on the distal segment and the measured displacement between the proximal segment and the distal segment.

In an Example 18, the catheter of Example 16, wherein the inductive sensing element is one of a plurality of inductive sensing elements, each of the plurality of inductive sensing elements being configured to measure displacement between the proximal segment and the distal segment.

In an Example 19, the catheter of Example 18, wherein the plurality of inductive sensing elements includes three inductive sensing elements arranged about a longitudinal axis of the catheter.

In an Example 20, the catheter of Example 18, wherein each of the plurality of inductive sensing elements is located within a central aperture of the spring.

In an Example 21, the catheter of Example 18, wherein the spring is one of a plurality of springs, and wherein each of the plurality of inductive sensing elements is located within a central aperture of one of the plurality of springs.

In an Example 22, the catheter of Example 16, wherein the inductive sensing element is oriented to measure displacement along a direction that is about parallel to a longitudinal axis of the catheter.

In an Example 23, the catheter of Example 16, wherein the inductive sensing element includes: a magnetic core; and conductive coil windings, the conductive coil windings being configured to move relative to the magnetic core in conjunction with movement between the distal segment and the proximal segment, wherein an inductance of the conductive coil windings changes based on its position relative to the magnetic core.

In an Example 24, the catheter of Example 23, wherein the magnetic core is substantially fixed relative to the distal segment, and wherein the conductive coil windings is substantially fixed relative to the proximal segment.

In an Example 25, the catheter of Example 23, wherein the inductive sensing element further includes an electrically insulating tube between the magnetic core and the conductive coil windings, wherein the conductive coil windings is mounted to the electrically insulating tube.

In an Example 26, the catheter of Example 25, wherein the conductive coil windings includes an electrical trace on the electrically insulating tube.

In an Example 27, the catheter of Example 23, wherein the conductive coil windings includes an insulating layer, wherein a least a portion of the insulating layer is adjacent to the magnetic core.

In an Example 28, the catheter of Example 23, further comprising a lubricating layer between the magnetic core and the conductive coil windings.

In an Example 29, the catheter of Example 16, wherein the distal segment includes an ablation element configured to deliver ablation therapy.

In an Example 30, a system for measuring a force comprises: a catheter comprising: a proximal segment; a distal segment, the catheter being configured to permit relative movement between the distal segment and the proximal segment in response to an application of force on the distal segment; and an inductive sensing element configured to measure displacement between the proximal segment and the distal segment; and control circuitry configured to receive a signal from the inductive sensing element indicative of the measured displacement and calculate a magnitude and a direction of force on the distal segment based on a known resistance to the application of force on the distal segment and the measured displacement between the proximal segment and the distal segment.

In an Example 31, the system of Example 30, wherein the inductive sensing element is one of a plurality of inductive sensing elements, each of the plurality of inductive sensing elements being configured to measure displacement between the proximal segment and the distal segment.

In an Example 32, the system of Example 31, wherein each of the plurality of inductive sensing elements is located within a central aperture of the spring.

In an Example 33, the system of Example 31, wherein the spring is one of a plurality of springs, and wherein each of the plurality of inductive sensing elements is located within a central aperture of one of the plurality of springs.

In an Example 34, the system of Example 30, wherein the distal segment includes an ablation element configured to deliver ablation therapy.

In an Example 35, a non-transitory computer readable medium comprises instructions for causing one or more programmable processors to: receive a signal from an inductive sensing element indicative of a measured displacement, the measured displacement representing relative movement between a proximal segment and a distal segment of a catheter in response to an application of force on the distal segment; calculate a magnitude and a direction of force on the distal segment based on a known resistance to the application of force on the distal segment and the measured displacement between the proximal segment and the distal segment; and output, in real time or approximately real time, indications of the magnitude and the direction of force to a user interface.

While multiple examples are disclosed, still other examples of the present disclosure will become apparent to those skilled in the art from the following detailed description, which shows and describes illustrative examples of this disclosure. Accordingly, the drawings and detailed description are to be regarded as illustrative in nature and not restrictive.

Figure 1A:
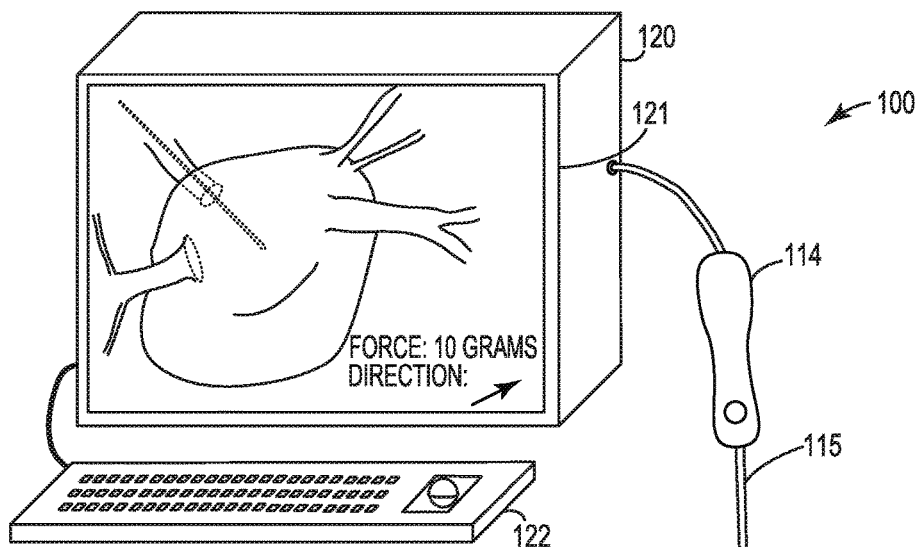
FIGS. 1A-1C illustrate a system for measuring a displacement with a catheter including an inductive sensing element configured to measure displacement between a proximal segment and a distal segment of the catheter, in accordance with embodiments of the disclosure.

While this disclosure is amenable to various modifications and alternative forms, specific examples have been shown by way of example in the drawings and are described in detail below. The intention, however, is not to limit this disclosure to the particular examples described. On the contrary, this disclosure is intended to cover all modifications, equivalents, and alternatives falling within the spirit of this disclosure as defined by the claims.

DETAILED DESCRIPTION

Various cardiac abnormalities can be attributed to improper electrical activity of cardiac tissue. Such improper electrical activity may include, but is not limited to, generation of electrical signals, conduction of electrical signals, and/or mechanical contraction of the tissue in a manner that does not support efficient and/or effective cardiac function. For example, an area of cardiac tissue may become electrically active prematurely or otherwise out of synchrony during the cardiac cycle, thereby causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactivate tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can lesion the tissue and prevent the tissue from improperly generating or conducting electrical signals. For example, a line, a circle, or other formation of lesioned cardiac tissue can block the propagation of errant electrical signals. In some cases, cardiac ablation is intended to cause the death of cardiac tissue and to have scar tissue reform over the lesion, where the scar tissue is not associated with the improper electrical activity. Lesioning therapies include electrical ablation, radiofrequency ablation, cyroablation, microwave ablation, laser ablation, and surgical ablation, among others. While cardiac ablation therapy is referenced herein as an exemplar, various examples of the present disclosure can be directed to ablation of other types of tissue and/or to non-ablation diagnostic and/or catheters that deliver other therapies.

Ablation therapy can be delivered in a minimally invasive manner, such as with a catheter introduced to the heart through a vessel, rather than surgically opening the heart for direct access (e.g., as in a maze surgical procedure). For example, a single catheter can be used to perform an electrophysiology study of the inner surfaces of a heart to identify electrical activation patterns. From these patterns, a clinician can identify areas of inappropriate electrical activity and ablate cardiac tissue in a manner to kill or isolate the tissue associated with the inappropriate electrical activation. However, the lack of direct access in a catheter-based procedure may require that the clinician only interact with the cardiac tissue through a single catheter and keep track of all of the information that the catheter collects or is otherwise associated with the procedure. In particular, it can be challenging to determine the location of the therapy element (e.g., the proximity to tissue), the quality of a lesion, and whether the tissue is fully lesioned, under-lesioned (e.g., still capable of generating and/or conducting unwanted electrical signals), or over-lesioned (e.g., burning through or otherwise weakening the cardiac wall). The quality of the lesion can depend on the degree of contact between the ablation element and the targeted tissue. For example, an ablation element that is barely contacting tissue may not be adequately positioned to deliver effective ablation therapy. Conversely, an ablation element that is pressed too hard into tissue may deliver too much ablation energy or cause a perforation.

The present disclosure concerns, among other things, methods, devices, and systems for assessing a degree of contact between a part of a catheter (e.g., an ablation element) and tissue. Knowing the degree of contact, such as the magnitude and the direction of a force generated by contact between the catheter and the tissue, can be useful in determining the degree of lesioning of the targeted tissue. Information regarding the degree of lesioning of cardiac tissue can be used to determine whether the tissue should be further lesioned or whether the tissue was successfully ablated, among other things. Additionally or alternatively, an indicator of contact can be useful when navigating the catheter because a user may not feel a force being exerted on the catheter from tissue as the catheter is advanced within a patient, thereby causing vascular or cardiac tissue damage or perforation.

Figure 1B:
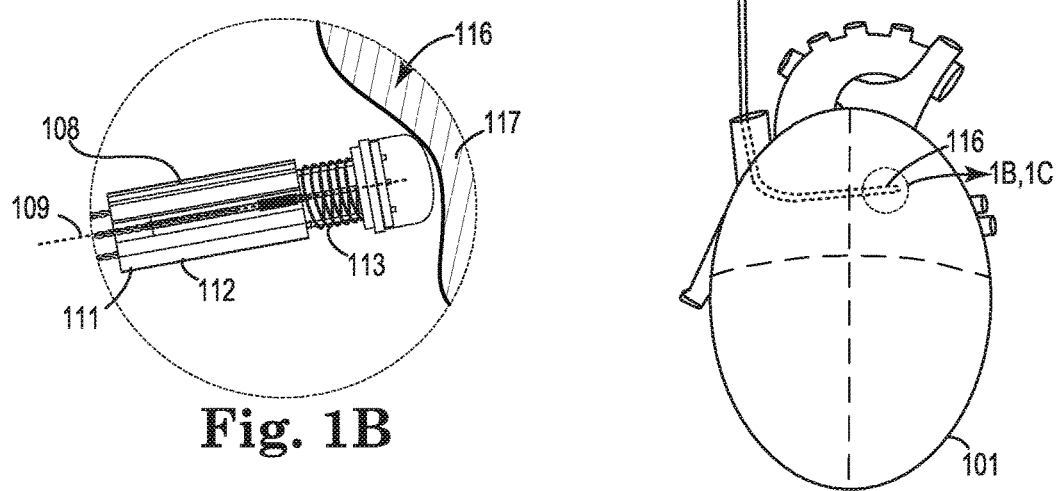
Figure 1C:
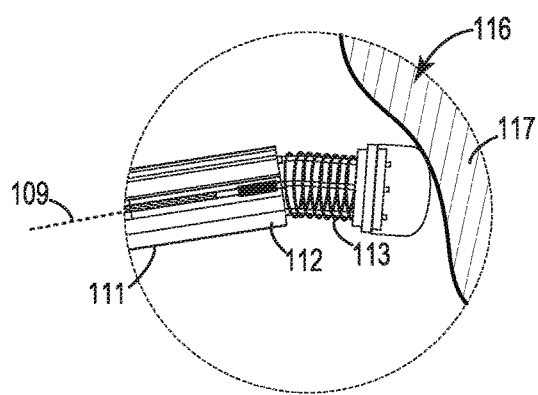

FIGS. 1A-1C illustrate an example of a system 100 for sensing data from inside the body and/or delivering therapy. For example, the system 100 can be configured to map cardiac tissue and/or ablate the cardiac tissue, among other options. The system 100 includes a catheter 110 connected to a control unit 120 via handle 114. The catheter 110 can comprise an elongated tubular member having a proximal end 115 connected with the handle 114 and a distal end 116 configured to be introduced within a heart 101 or other area of the body. As shown in FIG. 1A, the distal end 116 of the catheter 110 is within the left atrium.

As shown in FIG. 1B, the distal end 116 of the catheter 110 includes a proximal segment 111, a position sensing segment 112, and a distal segment 113. The proximal segment 111, the position sensing segment 112, and the distal segment 113 can be coaxially aligned with each other in a base orientation as shown in FIG. 1B. Specifically, each of the proximal segment 111, the position sensing segment 112, and the distal segment 113 are coaxially aligned with a common longitudinal axis 109. The longitudinal axis 109 can extend through the radial center of each of the proximal segment 111, the position sensing segment 112, and the distal segment 113, and can extend through the radial center of the distal end 116 as a whole. The proximal segment 111, the position sensing segment 112, and the distal segment 113 can be mechanically biased to assume the base orientation. In some examples, the coaxial alignment of the proximal segment 111 with the distal segment 113 can correspond to the base orientation. As shown, the distal end 116, at least along the proximal segment 111, the position sensing segment 112, and the distal segment 113, extends straight. In some examples, this straight arrangement of the proximal segment 111, the position sensing segment 112, and the distal segment 113 can correspond to the base orientation.

The distal segment 113, or any other segment, can be in the form of an electrode configured for sensing electrical activity, such as electrical cardiac signals. In other examples, such an electrode can additionally or alternatively be used to deliver ablative energy to tissue.

The catheter 110 includes force sensing capabilities. For example, as shown in FIGS. 1B and 1C, the catheter 110 is configured to sense a force due to engagement with tissue 117 of heart 101. The distal segment 113 can be relatively rigid while segments proximal of the distal segment 113 can be relatively flexible. In particular, the position sensing segment 112 may be more flexible than the distal segment 113 and the proximal segment 111 such that when the distal end 116 of the catheter 110 engages tissue 117, the position sensing segment 112 bends, as shown in FIG. 1C. For example, the distal end 116 of the catheter 110 can be generally straight as shown in FIG. 1B. When the distal segment 113 engages tissue 117, the distal end 116 of the catheter 110 can bend at the position sensing segment 112 such that the distal segment 113 moves relative to the proximal segment 111. As shown in FIGS. 1B and 1C, the normal force from the tissue moves the distal segment 113 out of coaxial alignment (e.g., with respect to the longitudinal axis 109) with the proximal segment 111 while the position sensing segment 112 bends. As such, proximal segment 111 and the distal segment 113 may be stiff to not bend due to the force while the position sensing segment 112 may be less stiff and bend to accommodate the force exerted on the distal end 116 of the catheter 110. One or more inductive sensing elements within the distal end 116 of the catheter 110 can sense the degree of bending of the position sensing segment 112 to determine the magnitude and the direction of the force, as further discussed herein.

The control unit 120 of the system 100 includes a display 121 (e.g., a liquid crystal display or a cathode ray tube) for displaying information. The control unit 120 further includes a user input 122 which may include one or more buttons, toggles, a track ball, a mouse, touchpad, or the like for receiving user input. The user input 122 can additionally or alternatively be located on the handle 114. The control unit 120 can contain control circuitry for performing the functions referenced herein. Some or all of the control circuitry can alternatively be located within the handle 114.

Figure 2:
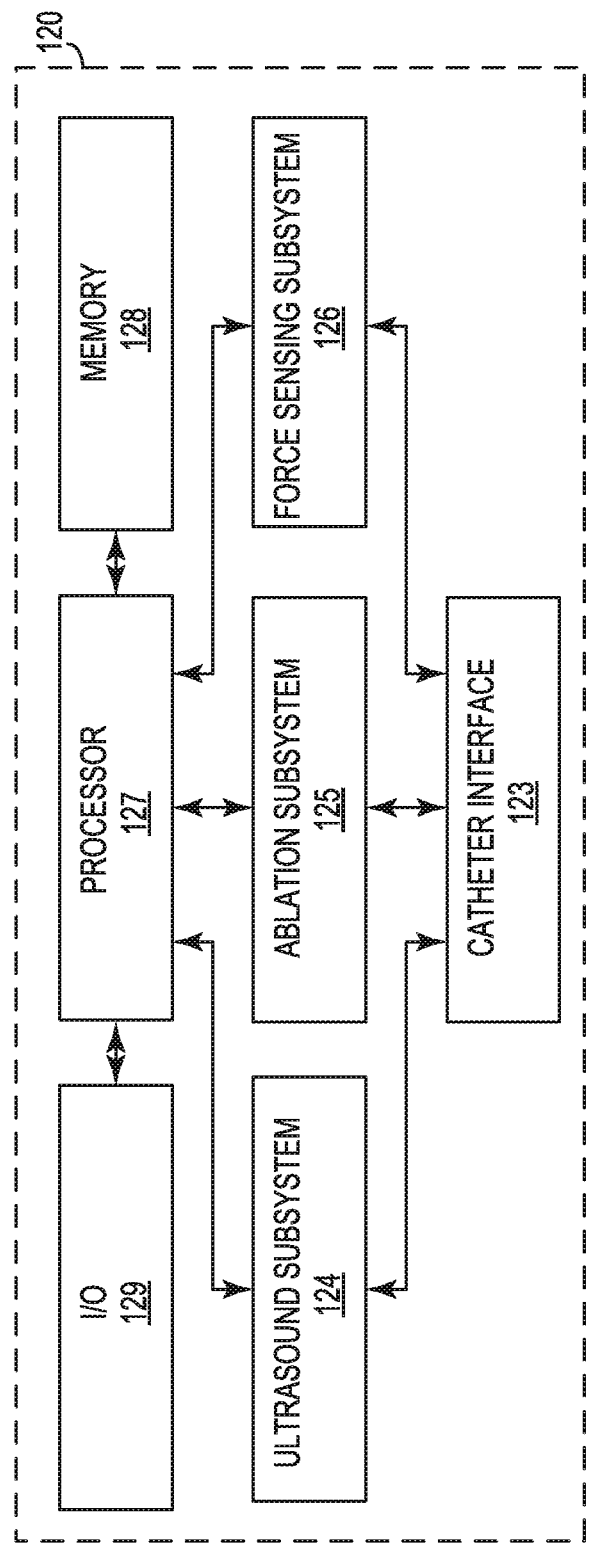
FIG. 2 is a block diagram of circuitry for controlling various functions of a catheter including an inductive sensing element, in accordance with embodiments of the disclosure.

FIG. 2 illustrates a block diagram showing an example of control circuitry which can perform functions referenced herein. This or other control circuitry can be housed within control unit 120, which can comprise a single housing or multiple housings among which components are distributed. Control circuitry can additionally or alternatively be housed within the handle 114. The components of the control unit 120 can be powered by a power supply (not shown), which supplies electrical power to any of the components of the control unit 120 and the system 100. The power supply can plug into an electrical outlet and/or provide power from a battery, among other options.

The control unit 120 may include a catheter interface 123. The catheter interface 123 may include a plug which receives a cord from the handle 114. The catheter 110 may include multiple conductors to convey electrical signals between the distal end 116 and the proximal end 115 and further to the catheter interface 123. It is through the catheter interface 123 that the control unit 120 (and/or the handle 114 if control circuitry is included in the handle 114) can send electrical signals to any element within the catheter 110 and/or receive an electrical signal from any element within the catheter 110. The catheter interface 123 can conduct signals to any of the components of the control unit 120.

The control unit 120 may include an ultrasound subsystem 124 which includes components for operating the ultrasound functions of the system 100. While the illustrated example of control circuitry shown in FIG. 2 includes the ultrasound subsystem 124, it will be understood that not all examples include ultrasound subsystem 124 or any circuitry for imaging tissue. The ultrasound subsystem 124 includes a signal generator configured to generate a signal for ultrasound transmission and signal processing components (e.g., a high pass filter) configured to filter and process reflected ultrasound signals as received by an ultrasound transducer in a sense mode and conducted to the ultrasound subsystem 124 through a conductor in the catheter 110. The ultrasound subsystem 124 can send signals to elements within the catheter 110 via the catheter interface 123 and/or receive signals from elements within the catheter 110 via the catheter interface 123.

The control unit 120 may include an ablation subsystem 125. The ablation subsystem 125 includes components for operating the ablation functions of the system 100. While the illustrated example of control circuitry shown in FIG. 2 includes the ablation subsystem, it will be understood that not all example may include ablation subsystem 125 or any circuitry for generating an ablation therapy. The ablation subsystem 125 includes an ablation generator to provide different therapeutic outputs depending on the particular configuration (e.g., a high frequency alternating current signal in the case of radiofrequency ablation to be output through one or more electrodes). Providing ablation energy to target sites is further described, for example, in U.S. Pat. Nos. 5,383,874 and 7,720,420, each of which is are incorporated by reference in its entirety for all purposes. The ablation subsystem 125 may support any other type of ablation therapy, such as microwave ablation. The ablation subsystem 125 can deliver signals or other type of ablation energy through the catheter interface 123 to the catheter 110.

The control unit 120 further includes a force sensing subsystem 126. The force sensing subsystem 126 include components for measuring a force experienced by the catheter 110. Such components may include signal processors, analog-to-digital converters, operational amplifiers, comparators, and/or any other circuitry for conditioning and measuring one or more signals. The force sensing subsystem 126 can send signals to elements within the catheter 110 via the catheter interface 123 and/or receive signals from elements within the catheter 110 via the catheter interface 123.

Each of the ultrasound subsystem 124, the ablation subsystem 125, and the force sensing subsystem 126 may send signals to, and receive signals from, the processor 127. The processor 127 may be any type of processor for executing computer functions. For example, the processor 127 can execute program instructions stored within the memory 128 to carry out any function referenced herein, such as determine the magnitude and direction of a force experienced by the catheter 110.

The control unit 120 further includes an input/output subsystem 129 which can support user input and output functionality via a connection to one or more user interfaces. For example, the input/output subsystem 129 may support the display 121 to display any information referenced herein, such as a graphic representation of tissue, the catheter 110, and a magnitude and direction of the force experienced by the catheter 110, amongst other options. In some examples, the display of such information may be in real time or approximately real time such that a clinician may receive active feedback regarding the positions and/or forces experienced by the catheter 110 during a surgical procedure, the active feedback being sufficient to allow the clinician to control the catheter to complete the procedure based on the active feedback provided by the display of the information in real time or approximately real time. Input/output subsystem 129 can log key and/or other input entries via the user input 122 and route the entries to other circuitry.

A single processor 127, or multiple processors, can perform the functions of one or more subsystems, and as such the subsystems may share control circuitry. Although different subsystems are presented herein, circuitry may be divided between a greater or lesser numbers of subsystems, which may be housed separately or together. In various examples, circuitry is not distributed between subsystems, but rather is provided as a unified computing system. Whether distributed or unified, the components can be electrically connected to coordinate and share resources to carry out functions.

Figure 3:
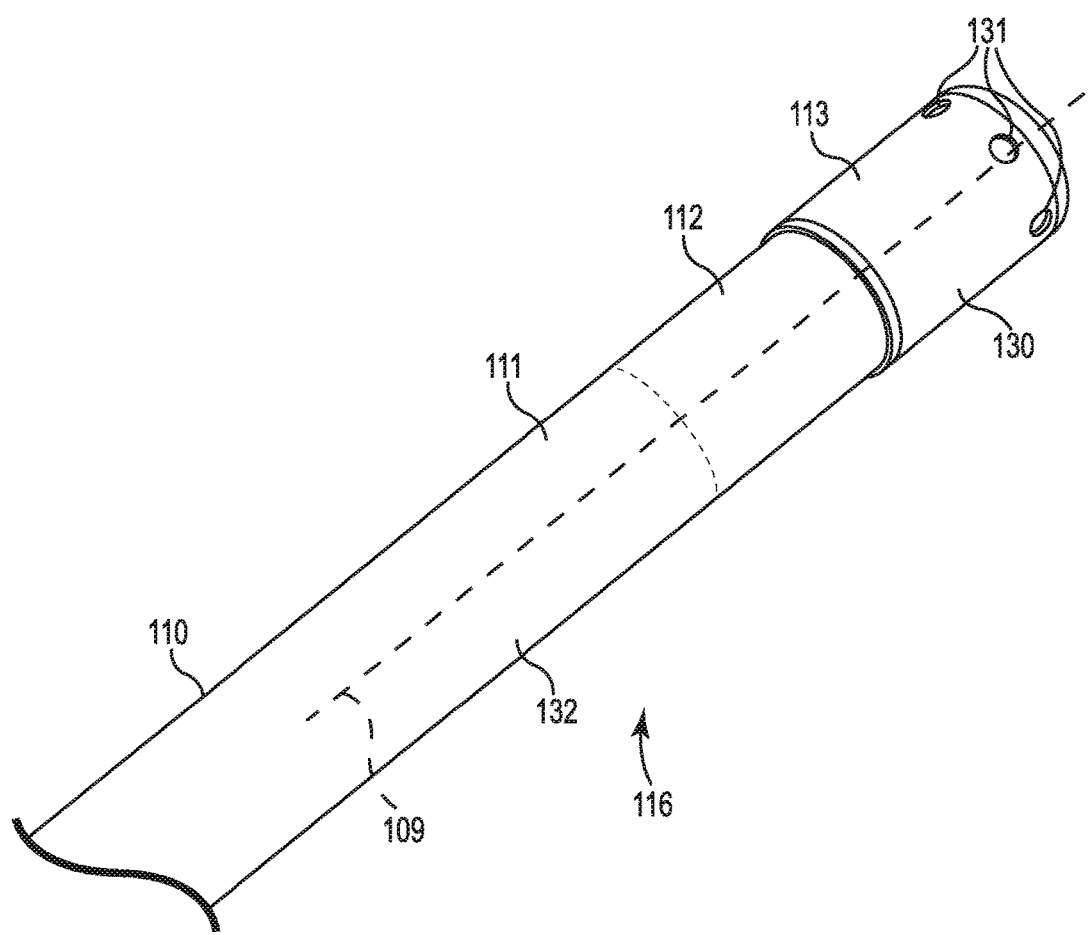
FIG. 3 is a perspective view of a distal end of a catheter including an inductive sensing element configured to measure displacement between a proximal segment and a distal segment of the catheter, in accordance with embodiments of the disclosure.

FIG. 3 illustrates a detailed view of the distal end 116 of the catheter 110. As illustrated in FIG. 3, catheter 110 includes a catheter shaft 132. The catheter shaft 132 can extend from the distal segment 113 to the handle 114 (FIG. 1A), and thus can define an exterior surface of the catheter 110 along the position sensing segment 112, the proximal segment 111, and further proximally to the proximal end 115 (FIG. 1A). The catheter shaft 132 can be a tube formed from various polymers, such as polyurethane, polyamide, polyether block amide, silicone, and/or other materials. In some examples, the catheter shaft 132 may be relatively flexible, and at least along the position sensing segment 112 may not provide any material mechanical support to the distal segment 113 (e.g., facilitated by thinning of the wall of the catheter shaft 132 along the position sensing segment 112).

As shown, the proximal segment 111 can be proximal and adjacent to the position sensing segment 112. The length of the proximal segment 111 can vary between different examples, and can be five millimeters to five centimeters, although different lengths are also possible. The length of the position sensing segment 112 can also vary between different examples and is dependent on the length of underlying features as will be further discussed herein. The position sensing segment 112 is adjacent to the distal segment 113. As shown in FIG. 3, the distal segment 113 can be defined by an electrode 130. The electrode 130 can be an ablation electrode. In some other examples, the distal segment 113 may not be an electrode. The electrode 130 can be in a shell form which can contain other components. The electrode 130 may include a plurality of ports 131. In some examples, the ports 131 may be fluidly connected to a source of irrigation fluid for flushing the volume adjacent to the distal segment 113. In some examples, one or more ultrasonic transducers, housed within the electrode 130, can transmit and receive signals through the ports 131 or through additional dedicated holes in the tip shell. Additionally or in place of the transducers, one or more miniature electrodes may be incorporated into the tip shell assembly.

Figure 4:
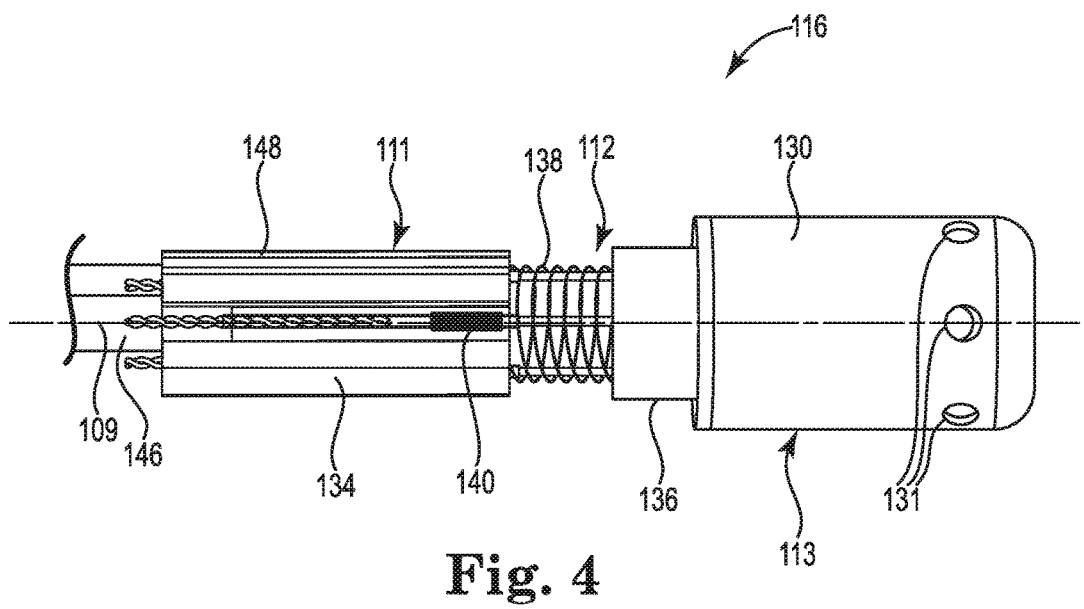
FIG. 4 is a cutaway view of a distal end of a catheter including am inductive sensing element configured to measure displacement between a proximal segment and a distal segment of the catheter, in accordance with embodiments of the disclosure.
Figure 5:
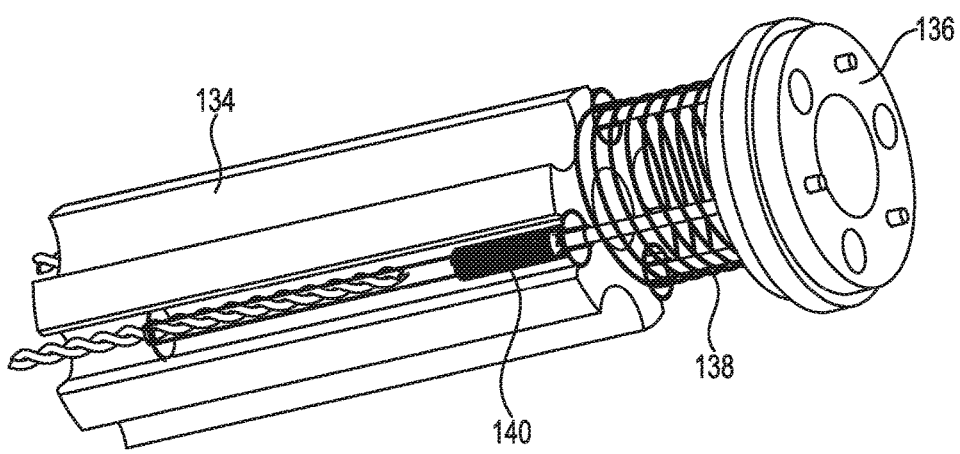
FIG. 5 illustrates an arrangement of inductive sensing elements for measuring displacement between a proximal segment and a distal segment of the catheter with a single spring between the proximal and distal segments, in accordance with embodiments of the disclosure.

FIG. 4 shows a side view of the inside of the distal end 116 of the catheter 110 of FIG. 3 after the removal of the catheter shaft 132 to expose various components that underlie the catheter shaft 132. FIG. 5 illustrates position sensing segment 112 including an arrangement of inductive sensing elements 140 for measuring displacement between proximal segment 134 and distal segment 136 of the catheter 110 with a single spring 138 between proximal segment 134 and distal segment 136.

As shown in FIG. 4, the proximal segment 111 may include a proximal hub 134, the distal segment 113 may include a distal hub 136, and the position sensing segment 112 may include one or more inductive sensing elements 140. The inductive sensing elements 140 extend between the proximal hub 134 and the distal hub 136 in order to measure displacement there between. The inductive sensing elements 140 are configured to output one more signals indicative of the relative movement between the proximal segment 111 and the distal segment 113.

One or both of the proximal hub 134 and the distal hub 136 can be formed from polymer materials, such as polyethylene, or PEEK, or can be formed from a metal, such as stainless steel. One or both of the proximal hub 134 and the distal hub 136 can be formed from a composite of metal, polymer, and/or other materials.

The inductive sensing elements 140 are located within a central aperture of the spring 138. The spring 138 provides a flexible structural connection between the proximal segment 111 and the distal segment 113. The spring 138 can be formed from a resilient material, for example, polymer materials, metals (e.g. stainless steel, nitinol), or other materials. In some examples, the spring 138 may be formed from a stainless steel hypotube, and may optionally include transverse slots designed to provide a desired bending resistance and/or desired range of motion.

The position information from inductive sensing elements 140, when combined with a known resistance to displacement, such a spring constant for spring 138, as well as catheter shaft 132, the displacement measurements from inductive sensing elements 140 also provide indications of contact force on the catheter tip. In addition, with an array of inductive sensing elements 140 arranged about common longitudinal axis 109, force direction information may also be calculated based on the relative motion of the different inductive sensing elements 140. For example, three or more inductive sensing elements 140 may be arranged about common longitudinal axis 109 to provide three-dimensional force information.

In some examples, one or more of inductive sensing elements 140 may be oriented to measure displacement along a direction that is about parallel to longitudinal axis 109. In other examples, one or more of inductive sensing elements 140 may be oriented to measure displacement along a direction that is angled relative to longitudinal axis 109. In either example, the mechanical configuration of the inductive sensing elements 140 relative to the proximal hub 134 and the distal hub 136 should be considering when determining the displacement measurements and contact force. In some particular examples, inductive sensing elements 140 may be configured to measure distances in increments of 1 micron or less over a range of about 1 millimeter. Of course, variations to the measured position increments and range may be made according to design requirements and are within the spirit of this disclosure.

In the base orientation, the proximal hub 134, the distal hub 136, and the spring 138 can be coaxially aligned with respect to the longitudinal axis 109, as shown in FIG. 4. For example, the longitudinal axis 109 can extend through the respective radial centers of each of the proximal hub 134, the distal hub 136, and the spring 138. An inner tube 146 can extend through the catheter 110 (e.g., from the handle 114, FIG. 1A), through the proximal hub 134, the spring 138, and the distal hub 136. The inner tube 146 may include one or more lumens within which one or more conductors (not illustrated) can extend from the proximal end 115 (FIG. 1A) to the distal segment 113, such as for connecting with one or more electrical elements (e.g., ultrasound transducer, electrode, stain sensor, or other component). Coolant fluid can additionally or alternatively be routed through the inner tube 146. In various examples, the catheter 110 is open irrigated (e.g., through the plurality of ports 131) to allow the coolant fluid to flow out of the distal segment 113. Various other examples concern a non-irrigated catheter 110.

A tether 148 can attach to a proximal end of the proximal hub 134. Considering FIGS. 1A and 4, together, the tether 148 can attach to a deflection mechanism within the handle 114 to cause deflection of the distal end 116. A knob, slider, or plunger on a handle 114 may be used to create tension or slack in the tether 148.

As shown in FIG. 4, the position sensing segment 112 can extend from a distal edge of the proximal hub 134 to a proximal edge of the distal hub 136. As such, the proximal hub 134 can be part of, and may even define the length of, the proximal segment 111 (FIG. 1A). Likewise, the distal hub 136 can be part of the distal segment 113. The position sensing segment 112 can be a relatively flexible portion that is mostly or entirely mechanically supported by the spring 138. As such, the proximal hub 134 and the distal hub 136 can be stiffer than the spring 138 such that a force directed on the distal segment 113 causes the distal end 116 to bend along the spring 138 rather than along the distal segment 113 or the proximal segment 111.

The structure of spring 138 may vary in different examples, and spring 138 may represent any spring with the correct dimensions requirements and spring constant such that force in the desired range may be measured. For example, spring 138 include helical coil, formed from an elongated material, such as a wire, flat strip or other shaped elongated material. In the same or different examples, spring 138 may include a tubular structure with transverse slots, such as perpendicular slots, and/or slanted slots. In the same or different examples, spring 138 may include multiple spring elements arranged in series or in parallel between proximal hub 134 and distal hub 136. In the same or different examples, spring 138 may provide a unidirectional resistance to bending forces or a direction-dependent resistance to bending forces. In this manner, the configuration of spring 138 may take any variety of suitable forms and constructions, and the configuration of spring 138 should not be limited to the particular examples of this disclosure.

Figure 6A:
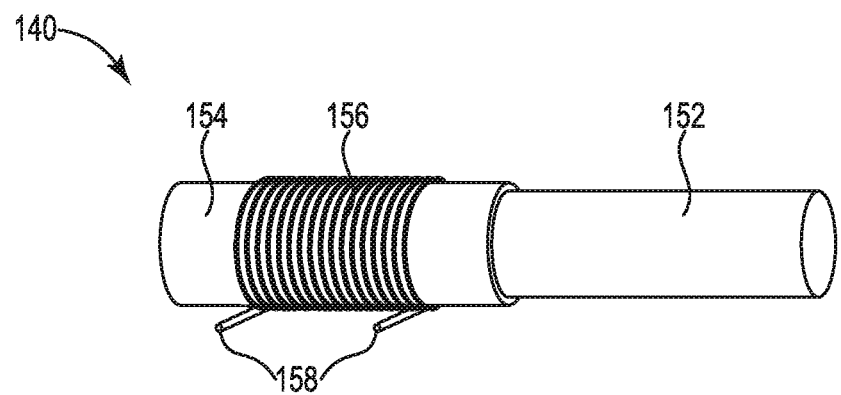
FIGS. 6A-6C illustrate an inductive sensing element at various sensing positions, in accordance with embodiments of the disclosure.
Figure 6B:
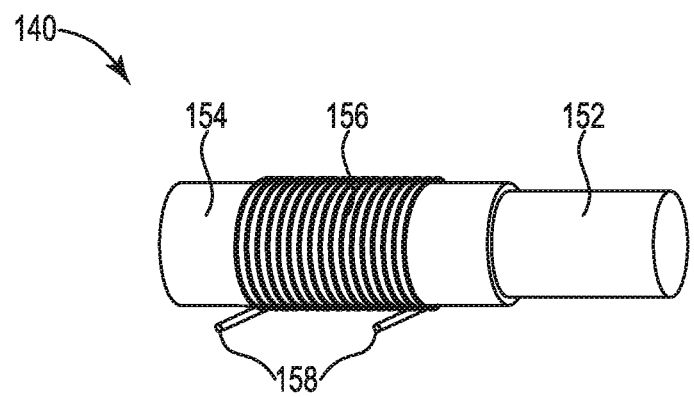
Figure 6C:
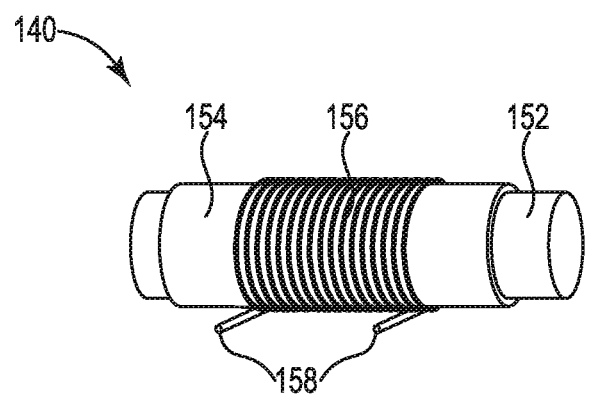

FIGS. 6A-6C illustrate inductive sensing element 140 at various sensing positions. More particularly, FIG. 6A illustrates inductive sensing element 140 at a relatively low inductance position, FIG. 6B illustrates inductive sensing element 140 at a medium inductance position, and FIG. 6C illustrates inductive sensing element 140 at a relatively high inductance position.

Inductive position sensor 140 includes three functional components, although the precise mechanical arrangement of these components may vary. Inductive position sensor 140 may be any type of inductive sensor including, for example, a flat coil, or a coil wound around a core. Specifically, inductive sensing element 140 includes magnetic core 152, coil windings 156 and insulating layer 154, which function to electrically insulate coil windings 156 and magnetic core 152. Inductive position sensor 140 may further include a lubricating layer between the coil windings 156 and magnetic core 152.

Magnetic core 152 includes a magnetic material, such as a ferromagnetic material. Magnetic core 152 may be a single piece or a multi-segment material.

Coil windings 156 form a set of windings of an elongated electrical conductor about magnetic core 152. Generally, coil windings 156 may be formed from an insulated wire, such as a copper wire. For example, the wire may be a copper wire with a gauge greater than 50 AWG. In other examples, coil windings 156 may represent an electrical trace printed or deposited on a substrate, such as insulating layer 154.

Insulating layer 154 functions to electrically separate coil windings 156 and magnetic core 152. In some examples, insulating layer 154 may include insulation on the wire of coil windings 156. Alternatively or additionally, insulating layer 154 may include a polymeric tube, such as Polyimide though other materials such as plastics, ceramics and metals may be used. For example, coil windings 156 may be mounted to the tube. In some such examples the length of the tube may be longer than coil windings 156 so that magnetic core 152 is coaxially constrained with coil windings 156 even when the position of magnetic core 152 does not overlap with coil windings 156 (FIG. 6a) only partially overlap with coil windings 156 (FIG. 6b). In the same or different examples, a relatively low permeability material may be affixed to one or both ends of magnetic core 152 to allow coil windings 156 to slide beyond the end of magnetic core 152 while remaining coaxially constrained with magnetic core 152.

In some examples, insulating layer 154 may double as a lubricating layer between the coil windings 156 and magnetic core 152. In the same or different examples, a lubricating substance may be applied between the coil windings 156 and magnetic core 152 to mitigate friction during movement of coil windings 156 relative to magnetic core 152.

Inductive position sensor 140 may further include an optional layer protecting the outside of coil windings 156 as the elongated conductor of coil windings 156 may be somewhat fragile.

Inductive position sensor 140 provides a detectable inductance via leads 158 of coil windings 156 based on the relative positions of coil windings 156 and magnetic core 152. For example, the inductance L provided by coil windings 156 is defined by Equation 1 below, wherein n=number of turns, A=area of core, l=length of the coil, µ=permeability of core:

$$L = \mu * n^2 * A / l \quad \text{(Equation 1)}$$

However, the permeability of the core varies according to the material within the core of the coil. For example, the relative permeability of air is approximately 1, whereas the relative permeability of iron is approximately 5000. For this reason, when magnetic core 152 fills the entire coil volume of coil windings 156 (FIG. 6c), inductive sensing element 140 provides a relatively high inductance. In contrast, when magnetic core 152 is completely outside the entire coil volume of coil windings 156 (FIG. 6a), inductive sensing element 140 provides a relatively low inductance. With magnetic core 152 partly within the coil volume of coil windings 156 (FIG. 6b), inductive sensing element 140 provides an inductance that varies according to the proportion of magnetic core 152 located within the coil volume of coil windings 156. In this manner, by detecting the inductance from leads 158 of coil windings 156, the precise position of coil windings 156 relative to magnetic core 152 may be determined, e.g., by processor 127 and force sensing subsystem 126 (FIG. 2).

In this manner, inductive sensing element 140 provides a change in inductance of coil windings 156 as magnetic core 152 is moved into and out of the annulus of coil windings 156. In the particular example of FIG. 6a, magnetic core 152 is positioned just outside the annulus of coil windings 156 but still within a tube forming insulating layer 154. In this state there is minimal interaction of magnetic core 152 with the magnetic field of coil windings 156 to provide a relatively low inductance. In the particular example of FIG. 6b a significant portion of magnetic core 152 has moved into the annulus of coil windings 165 resulting in significant magnetic interactions between magnetic core 152 and coil windings 165 to provide a medium level of inductance. Finally, in the particular example of FIG. 6c magnetic core 152 is protruding out of both ends of coil windings 165 and magnetic interactions between magnetic core 152 and coil windings 165 are high yielding the state of greatest inductance.

The coil windings 156 may be configured to move relative to the magnetic core 152 in conjunction with movement between the distal segment 136 and the proximal segment 134, wherein an inductance of the proximal segment 134 changes based on its position relative to magnetic core 152. In some examples, coil windings 156 may be substantially fixed relative to the proximal segment 134, whereas magnetic core 152 may be substantially fixed relative to distal segment 136 of the catheter 110. For example, substantially fixing coil windings 156 to the proximal segment 134 may facilitate an easier connection to leads 158 from the proximal end of the catheter 110. In other examples, one or more of coil windings 156 may be substantially fixed relative to the distal segment 136, with corresponding magnetic cores 152 being substantially fixed relative to proximal segment 134 of the catheter 110.

Figure 7:
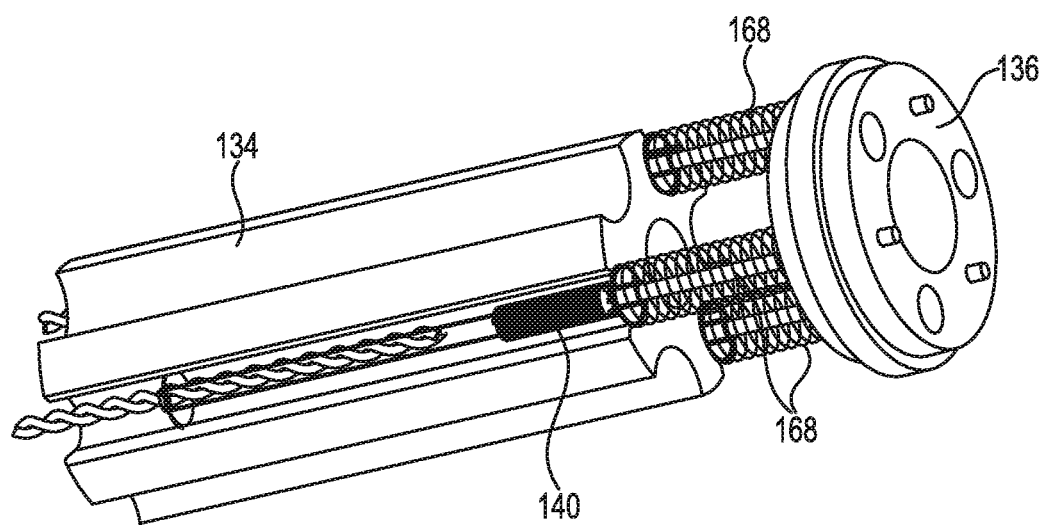
FIG. 7 illustrates an arrangement of inductive sensing elements for measuring displacement between a proximal segment and a distal segment of the catheter with springs surrounding each of inductive sensing elements in the arrangement, in accordance with embodiments of the disclosure.

FIG. 7 illustrates position sensing segment 162, which represents an alternative to position sensing segment 112 (FIG. 5). Like position sensing segment 112, position sensing segment 162 includes an arrangement of inductive sensing elements 140 for measuring displacement between proximal segment 134 and distal segment 136 of the catheter 110. In contrast to position sensing segment 112 position sensing segment 162 includes a plurality of springs 168, with one of the inductive sensing elements 140 being located within the central aperture of one of the springs 168 such that one of the springs 168 surround each of inductive sensing elements 140. Like-numbered elements of position sensing segment 162 should be considered the same or similar to the corresponding like-numbered elements of position sensing segment 112. For brevity, details described with respect to position sensing segment 112 that are the same or similar to position sensing segment 162 are described in limited or no detail with respect to position sensing segment 162.

Springs 168 provide a flexible structural connection between the proximal segment 111 and the distal segment 113. The springs 168 may each be formed from a resilient material, for example, polymer materials, metals (e.g. stainless steel, nitinol), or other materials. In some examples, the springs 168 may each be formed from a stainless steel hypotube, and may optionally include transverse slots designed to provide a desired bending resistance and/or desired range of motion.

The position information from inductive sensing elements 140, when combined with a known resistance to displacement, such spring constants for springs 168, as well as catheter shaft 132 (FIG. 3), the displacement measurements from inductive sensing elements 140 also provide indications of contact force on the catheter tip. In addition, with an array of inductive sensing elements 140 arranged about common longitudinal axis, force direction information may also be calculated based on the relative motion of the different inductive sensing elements 140. For example, three or more inductive sensing elements 140 may be arranged about common longitudinal axis to provide three-dimensional force information.

As shown in FIG. 7, the position sensing segment 162 can extend from a distal edge of the proximal hub 134 to a proximal edge of the distal hub 136. As such, the proximal hub 134 can be part of, and may even define the length of, the proximal segment 111 (FIG. 1A). Likewise, the distal hub 136 can be part of the distal segment 113. The position sensing segment 162 can be a relatively flexible portion that is mostly or entirely mechanically supported by the springs 168. As such, the proximal hub 134 and the distal hub 136 can be stiffer than the springs 168 such that a force directed on the distal segment 113 causes the distal end 116 to bend along the springs 168 rather than along the distal segment 113 or the proximal segment 111.

The structure of springs 168 may vary in different examples. Each of springs 168 may represent any spring with the correct dimensions requirements and spring constant such that force in the desired range may be measured. For example, one or more of springs 168 may include a helical coil, formed from an elongated material, such as a wire, flat strip or other shaped elongated material. In the same or different examples, one or more of springs 168 may include a tubular structure with transverse slots, such as perpendicular slots, and/or slanted slots. In the same or different examples, one or more of springs 168 may include multiple spring elements arranged in series or in parallel between proximal hub 134 and distal hub 136. In the same or different examples, one or more of springs 168 may provide a unidirectional resistance to bending forces or a direction-dependent resistance to bending forces. In addition, springs 168 may each be of substantially identical construction to each other or individual springs 168 may provide a unique construction relative to one or more other springs 168. In this manner, the configuration of springs 168 may take any variety of suitable forms and constructions, and the configuration of springs 168 should not be limited to the particular examples of this disclosure.

Various techniques disclosed herein may be implemented by computer program instructions. These program instructions may be provided to a processor, such as processor 127. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor. In addition, one or more processes may also be performed concurrently with other processes, or even in a different sequence from that illustrated without departing from the scope or spirit of the invention.

The computer program instructions can be stored on any suitable computer-readable medium (including any non-transitory computer-readable medium) including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device, such as control unit 120.

Various modifications and additions can be made to the exemplary examples discussed without departing from the scope of the present disclosure. For example, while the examples described above refer to particular features, the scope of this disclosure also includes examples having different combinations of features and examples that do not include all of the described features. Accordingly, the scope of the present disclosure is intended to embrace all such alternatives, modifications, and variations as fall within the scope of the claims, together with all equivalents thereof.

What is claimed is:

1. A catheter comprising:
a proximal segment;

a distal segment, the catheter being configured to permit relative movement between the distal segment and the proximal segment in response to an application of force on the distal segment; and an inductive sensing element configured to measure displacement between the proximal segment and the distal segment, wherein the inductive sensing element comprises:
conductive coil windings;
a magnetic core partially received within the conductive coil windings; and
an electrically insulating tube between the magnetic core and the conductive coil windings, wherein the conductive coil windings is mounted to the electrically insulating tube, and wherein the tube has a length that is longer than the length of the conductive coil windings such that the magnetic core is coaxially constrained within the coil windings,
wherein the conductive coil windings are configured to move relative to the magnetic core in conjunction with movement between the distal segment and the proximal segment, wherein an inductance of the conductive coil windings changes based on its position relative to the magnetic core.

2. The catheter of claim 1, further comprising a spring between the proximal segment and the distal segment, wherein the inductive sensing element is configured to measure force on the distal segment based on a known resistance to the application of force on the distal segment and the measured displacement between the proximal segment and the distal segment.

3. The catheter of claim 1, wherein the inductive sensing element is one of a plurality of inductive sensing elements, each of the plurality of inductive sensing elements being configured to measure displacement between the proximal segment and the distal segment.

4. The catheter of claim 3, wherein the plurality of inductive sensing elements includes three inductive sensing elements arranged about a longitudinal axis of the catheter.

5. The catheter of claim 3, wherein each of the plurality of inductive sensing elements is located within a central aperture of the spring.

6. The catheter of claim 3,
wherein the spring is one of a plurality of springs, and
wherein each of the plurality of inductive sensing elements is located within a central aperture of one of the plurality of springs.

7. The catheter of claim 1, wherein the inductive sensing element is oriented to measure displacement along a direction that is about parallel to a longitudinal axis of the catheter.

8. The catheter of claim 1,
wherein the magnetic core is substantially fixed relative to the distal segment, and
wherein the conductive coil windings is substantially fixed relative to the proximal segment.

9. The catheter of claim 1, wherein the conductive coil windings includes an electrical trace on the electrically insulating tube.

10. The catheter of claim 1, further comprising a lubricating layer between the magnetic core and the conductive coil windings.

11. The catheter of claim 1, wherein the distal segment includes an ablation element configured to deliver ablation therapy.

12. A system for measuring a force, the system comprising:

a catheter comprising:
a proximal segment;
a distal segment, the catheter being configured to permit relative movement between the distal segment and the proximal segment in response to an application of force on the distal segment; and
an inductive sensing element configured to measure displacement between the proximal segment and the distal segment, wherein the inductive sensing element comprises:
conductive coil windings;
a magnetic core partially received within the conductive coil windings; and
an electrically insulating tube between the magnetic core and the conductive coil windings, wherein the conductive coil windings is mounted to the electrically insulating tube, and wherein the tube has a length that is longer than the length of the conductive coil windings such that the magnetic core is coaxially constrained within the coil windings,
wherein the conductive coil windings are configured to move relative to the magnetic core in conjunction with movement between the distal segment and the proximal segment, wherein an inductance of the conductive coil windings changes based on its position relative to the magnetic core; and
control circuitry configured to receive a signal from the inductive sensing element indicative of the measured displacement and calculate a magnitude and a direction of force on the distal segment based on a known resistance to the application of force on the distal segment and the measured displacement between the proximal segment and the distal segment.

13. The system of claim 12, wherein the inductive sensing element is one of a plurality of inductive sensing elements, each of the plurality of inductive sensing elements being configured to measure displacement between the proximal segment and the distal segment.

14. The system of claim 13, wherein each of the plurality of inductive sensing elements is located within a central aperture of the spring.

15. The system of claim 13,
wherein the spring is one of a plurality of springs, and
wherein each of the plurality of inductive sensing elements is located within a central aperture of one of the plurality of springs.

16. The system of claim 12, wherein the distal segment includes an ablation element configured to deliver ablation therapy.

17. A non-transitory computer readable medium comprising instructions for causing one or more programmable processors to:
receive a signal from an inductive sensing element indicative of a measured displacement, the measured displacement representing relative movement between a proximal segment and a distal segment of a catheter in response to an application of force on the distal segment, the relative movement between the proximal segment and the distal segment of the catheter corresponding to the relative movement between a conductive coil windings of the inductive sensing element and a magnetic core coaxially constrained within an insulating tube about which th conductive coil windings are wrapped;
calculate a magnitude and a direction of force on the distal segment based on a known resistance to the application of force on the distal segment and the measured displacement between the proximal segment and the distal segment; and output, in real time or approximately real time, indications of the magnitude and the direction of force to a user interface.

\* \* \* \* \*